United States Patent
Taniguchi

(10) Patent No.: US 11,529,117 B2
(45) Date of Patent: Dec. 20, 2022

(54) ULTRASOUND DIAGNOSTIC APPARATUS, ULTRASOUND DIAGNOSTIC METHOD AND ULTRASOUND PROBE

(71) Applicant: Konica Minolta, Inc., Tokyo (JP)

(72) Inventor: Tetsuya Taniguchi, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 330 days.

(21) Appl. No.: 16/460,220

(22) Filed: Jul. 2, 2019

(65) Prior Publication Data
US 2020/0015776 A1 Jan. 16, 2020

(30) Foreign Application Priority Data
Jul. 13, 2018 (JP) .............................. JP2018-133298

(51) Int. Cl.
*A61B 8/08* (2006.01)
*A61B 8/00* (2006.01)

(52) U.S. Cl.
CPC .......... *A61B 8/0841* (2013.01); *A61B 8/4455* (2013.01); *A61B 8/4488* (2013.01); *A61B 8/463* (2013.01); *A61B 8/5246* (2013.01)

(58) Field of Classification Search
CPC ..... A61B 8/0841; A61B 8/463; A61B 8/4488; A61B 8/4455; A61B 8/5246; A61B 8/5253; A61B 8/4444; A61B 8/4472; G01S 7/5202; G01S 7/52073; G01S 7/52038; G01S 7/52079; G01S 15/8915
See application file for complete search history.

(56) References Cited

U.S. PATENT DOCUMENTS

| 5,083,568 | A * | 1/1992 | Shimazaki | G10K 11/345 600/459 |
| 8,454,516 | B1 * | 6/2013 | Roundhill | G01S 7/52077 600/407 |
| 9,307,954 | B2 * | 4/2016 | Nishigaki | A61B 8/4477 |

(Continued)

FOREIGN PATENT DOCUMENTS

| JP | 2003019133 A | 1/2003 |
| WO | 2017029830 A1 | 2/2017 |

OTHER PUBLICATIONS

Starkoff, "Ultrasound physical principles in today's technology," Australian Journal of Ultrasound in Medicine vol. 17 iss. 1, Feb. 2014, p. 4-10 (Year: 2014).*

(Continued)

*Primary Examiner* — Baisakhi Roy
(74) *Attorney, Agent, or Firm* — Lucas & Mercanti, LLP

(57) ABSTRACT

An ultrasound diagnostic apparatus includes a hardware processor that generates a first B mode image and a second B mode image on the basis of a first reception signal and a second reception signal whose beam width in the slice direction is narrower than the first reception signal, displays a display image on a display section, determines whether the end of the puncture needle in the display image is the actual needle point, and presents the determination result. The hardware processor presents the determination result on the basis of the first puncture needle image included in the first B mode image and the second puncture needle image included in the second B mode image.

15 Claims, 10 Drawing Sheets

(56) References Cited

U.S. PATENT DOCUMENTS

| | | | | |
|---|---|---|---|---|
| 2006/0074313 A1* | 4/2006 | Slayton | | A61N 7/00 600/439 |
| 2006/0241451 A1* | 10/2006 | Nakaya | | A61B 8/463 600/443 |
| 2007/0197914 A1* | 8/2007 | Kosaku | | A61B 17/3403 600/459 |
| 2009/0187104 A1* | 7/2009 | Yamagata | | A61B 8/0841 600/443 |
| 2012/0078103 A1* | 3/2012 | Tashiro | | A61B 8/463 600/443 |
| 2013/0096430 A1* | 4/2013 | Yoshiara | | A61B 8/463 600/438 |
| 2015/0094569 A1* | 4/2015 | Ohuchi | | A61B 8/0841 600/424 |
| 2015/0223776 A1* | 8/2015 | Ohuchi | | A61B 8/5246 600/424 |
| 2015/0342561 A1* | 12/2015 | Takeda | | A61B 8/0841 600/443 |
| 2016/0038770 A1* | 2/2016 | Tyler | | A61N 7/02 601/2 |
| 2016/0113624 A1* | 4/2016 | Katsuyama | | G01S 7/52028 600/437 |
| 2017/0172547 A1* | 6/2017 | Ito | | A61B 8/5269 |
| 2019/0307421 A1* | 10/2019 | Yamamoto | | A61B 8/463 |
| 2020/0027199 A1* | 1/2020 | Fujii | | G06T 5/002 |

OTHER PUBLICATIONS

Clevert et al., "Value of Tissue Harmonic Imaging (THI) and Contrast Harmonic Imaging (CHI) in detection and characterization of breat tumours", Eur Radiol vol. 17, 2007, p. 1-10 (Year: 2007).*

Anvari et al., "A Primer on the Physical Principles of Tissue Harmonic Imaging", RadioGraphics vol. 35 No. 7, 2015, p. 1955-1964 (Year: 2015).*

* cited by examiner

ULTRASOUND RADIATION SIDE

SLICE DIRECTION   SCAN DIRECTION

SLICE DIRECTION

ULTRASOUND DIAGNOSTIC APPARATUS, ULTRASOUND DIAGNOSTIC METHOD AND ULTRASOUND PROBE

CROSS REFERENCE TO RELATED APPLICATIONS

The entire disclosure of Japanese Patent Application No. 2018-133298 filed on Jul. 13, 2018 is incorporated herein by reference in its entirety.

BACKGROUND

Technological Field

The present invention relates to an ultrasound diagnostic apparatus, an ultrasound image display method and an ultrasound probe, and in particular the present invention relates to a technique that is usable in a case where a puncture needle is punctured into a target in a subject.

Description of the Related Art

As a conventionally known medical image diagnosis apparatus, there is a medical image diagnosis apparatus that visualizes shapes, properties or dynamics in a subject in the form of an ultrasound image by transmitting ultrasound to a subject and receiving reflection wave so as to perform a predetermined signal process on the reception signal. Ultrasound diagnostic apparatuses can acquire ultrasound images by simply attaching an ultrasound probe to the body surface and inserting an ultrasound probe into the body, and therefore are safe, and damage to the subject is small.

Ultrasound diagnostic apparatuses are used also for performing diagnosis of a body tissue by inserting a puncture needle into the patient's body as a subject to collect a tissue and/or bodily fluid, and for performing treatment with a puncture needle. In such diagnosis or treatment, an operator, e.g. a doctor can perform puncturing while confirming the position of the puncture needle and the position of the puncturing portion (target) by visually recognizing the ultrasound image obtained by the ultrasound diagnostic apparatus. Here, the puncture needle includes a medical needle and a medical device such as a catheter configured to be inserted into the subject.

When performing puncturing with use of an ultrasound diagnostic apparatus, it is preferable that the puncture needle and the target be clearly reflected in the ultrasound image (B mode image) in view of correctly performing the puncturing.

Conventionally, a tissue harmonic imaging (THI) method is known in which, by utilizing nonlinearity of ultrasound propagating in a tissue, harmonic components (e.g., frequencies 2f0 and 3f0) of received ultrasound (ultrasound echo) obtained by transmission of ultrasound having a center frequency of f0 are visualized in the form of an image.

In the THI method, since the harmonic generation depends on the non-linearly of the sound pressure, the beam width in the slice direction (hereinafter referred to as "slice width") of a beam profile presented by the harmonic component of a reception ultrasound is narrower than that of the beam profile presented by fundamental component, and thus high resolution and clear ultrasound image can be achieved. On the other hand, in puncturing, the puncture needle tends to be easily deviated in the slice direction with respect to the detection region of the harmonic component, and consequently sophisticated manipulation by the operator is required in order to determine the entire image of the puncture needle, in particular, the needle point.

Even in the case where a puncture needle guide or the like is used for assisting such puncturing, the advancing direction of the puncture needle is bent due to differences in shape and/or direction of the boundary of a tissue such as fascia, and/or difference in hardness of tissues due to nonhomogeneity of living body, and the needle point may be deviated from the detection region, thus leaving a room for improvement in ensuring determination of a needle point.

To solve such problems, WO2017/029830 discloses an ultrasound diagnostic apparatus using a THI method to display a harmonic image based on a harmonic component of a reception ultrasound and a needle image based on a fundamental component of a reception ultrasound in a synthesizing manner. An ultrasound image based on a fundamental component provides poorer image quality than an ultrasound image based on a harmonic component, but provides a wide detection region in the slice direction and a large amount of depth information, and thus can easily determine the entire image of the puncture needle.

In addition, Japanese Patent Application Laid-Open No. 2003-019133 discloses an ultrasound diagnostic apparatus that uses an ultrasound probe (a so-called multiple-line probe) in which a transducer is divided in the slice direction such that transducers are disposed in multiple lines in the scanning direction to change the color tone of a puncture needle image included in an ultrasound image obtained by the transducer group of each line, thus allowing for determination of the position of puncture needle in the slice direction. Note that, typically, an ultrasound probe (a so-called single-line probe) including transducers disposed in a single line is cheaper and more applicable than a multiple-line probe.

However, when the needle point of the puncture needle deviated in the slice direction from the detection region of the fundamental component, the ultrasound image obtained with the ultrasound diagnostic apparatus disclosed in WO2017/029830 does not include the entire image of the puncture needle. Therefore, the operator has to determine whether the end of the puncture needle image included in the ultrasound image is the actual needle point or is a depiction of a middle portion of puncture needle, and as such considerable experience and high skill are required for precise determination.

While the ultrasound diagnostic apparatus disclosed in Japanese Patent Application Laid-Open No. 2003-019133 can surely determine whether the end of the puncture needle included in the ultrasound image is the actual needle point when the position of the puncture needle is close to the puncturing point, the cost of the ultrasound probe and the device is high with the multiple-line probe.

SUMMARY

An object of the present invention is to provide an ultrasound diagnostic apparatus, an ultrasound image display method and an ultrasound probe that can use inexpensive and highly applicable single-line probe and can easily determine the end of the puncture needle in the display image.

Note that, in the present invention, the puncture needle is not limited to so-called injection needles used for chemical liquid injection cell diagnosis, and may include a living body insertion device such as a catheter. Further, the structure thereof is not limited to a lumen structure, and may be needles, such as acupuncture needles, provided with no lumen structure for injection of chemical liquid.

An ultrasound diagnostic apparatus according to the present invention transmits ultrasound to a subject through an ultrasound probe in which a plurality of transducers are disposed in a single line in a scanning direction and receives a reflection wave reflected in the subject to generate and display an ultrasound image, the ultrasound diagnostic apparatus including a hardware processor configured to acquire a first reception signal and a second reception signal from a reception signal obtained by the ultrasound probe; generate a first B mode image and a second B mode image on a basis of the first reception signal and the second reception signal; display a display image on a display section on a basis of the first B mode image and the second B mode image; determine whether an end of a puncture needle in the display image is an actual end of the puncture needle when the puncture needle is inserted into the subject; and present a determination result. A beam width in a slice direction of a second beam profile indicated by the second reception signal is narrower than that of a first beam profile indicated by the first reception signal, and the hardware processor presents the determination result on a basis of a first puncture needle image included in the first B mode image and a second puncture needle image included in the second B mode image.

An ultrasound image display method according to the present invention is a method in which ultrasound is transmitted to a subject through an ultrasound probe in which a plurality of transducers are disposed in a single line in a scanning direction, and a reflection wave reflected in the subject is received to generate and display an ultrasound image, the method including: acquiring a first reception signal and a second reception signal from a reception signal obtained by the ultrasound probe; generating a first B mode image and a second B mode image on a basis of the first reception signal and the second reception signal; displaying a display image on a display section on a basis of the first B mode image and the second B mode image; determining whether an end of a puncture needle in the display image is an actual end of the puncture needle when the puncture needle is inserted into the subject; and presenting a determination result of the determining. A beam width in a slice direction of a second beam profile indicated by the second reception signal is narrower than a first beam profile indicated by the first reception signal, and in the presenting, the determination result is presented on a basis of a first puncture needle image included in the first B mode image and a second puncture needle image included in the second B mode image.

An ultrasound probe according to the present invention is configured to transmit and receive ultrasound, the ultrasound probe including: a transducer array in which a plurality of transducers are disposed in a single line in a scanning direction; an acoustic lens disposed on an ultrasound radiation side of the transducer array; and a curvature of a radiation surface of the acoustic lens is discontinuous between a center portion and an end portion of the radiation surface in a slice direction.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

Figure 1:
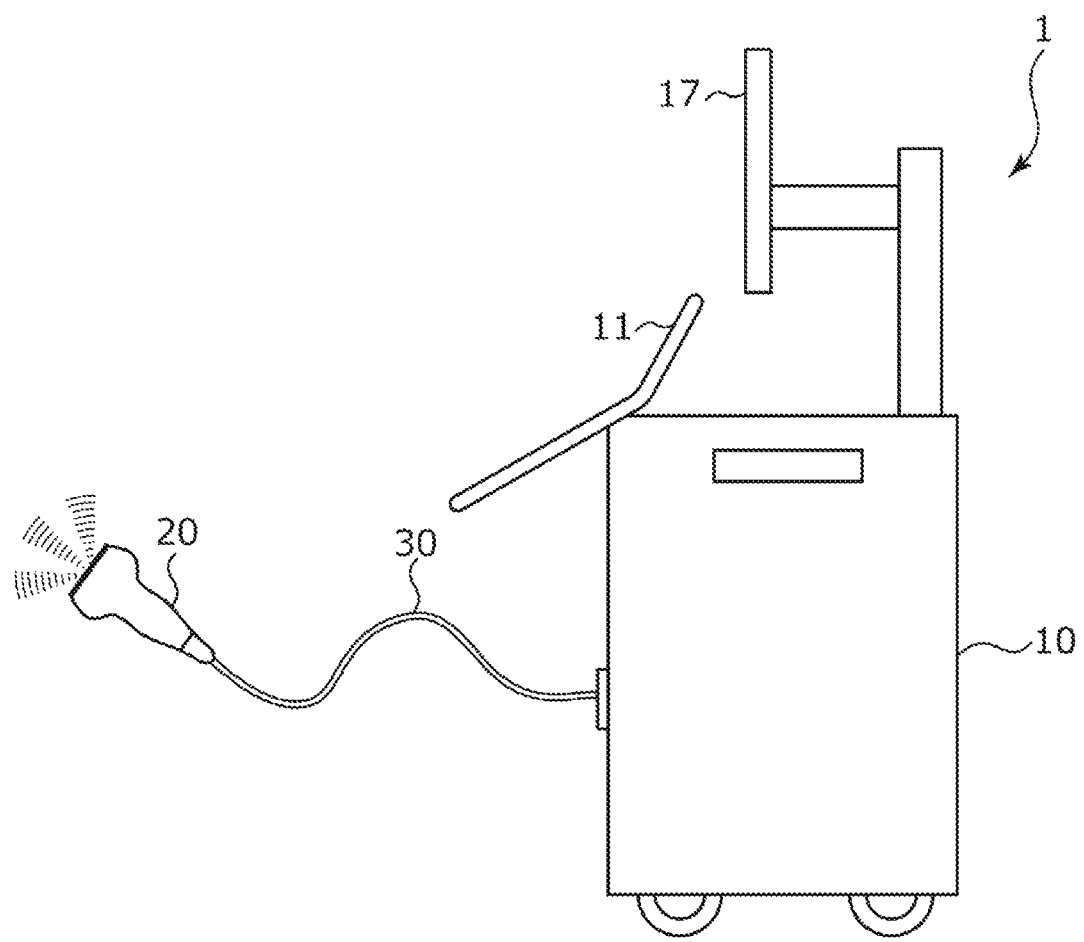
FIG. 1 illustrates an external appearance of an ultrasound diagnostic apparatus according to an embodiment.
Figure 2A:
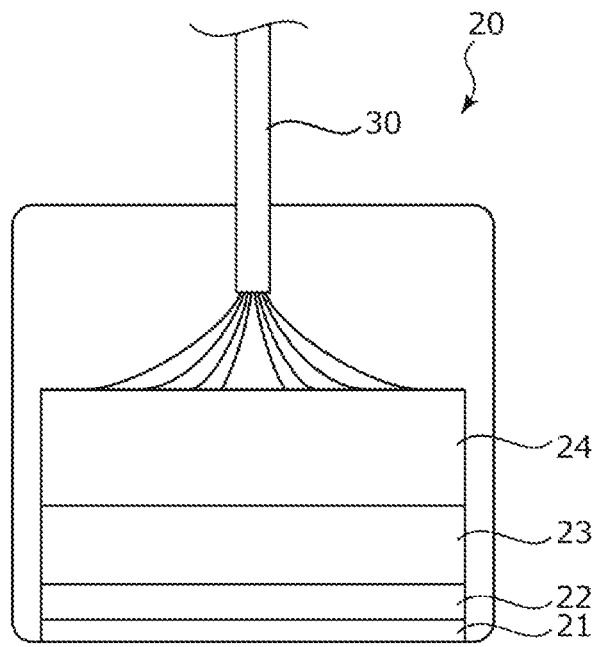
FIG. 2A and FIG. 2B illustrate a configuration of an ultrasound probe.
Figure 2B:
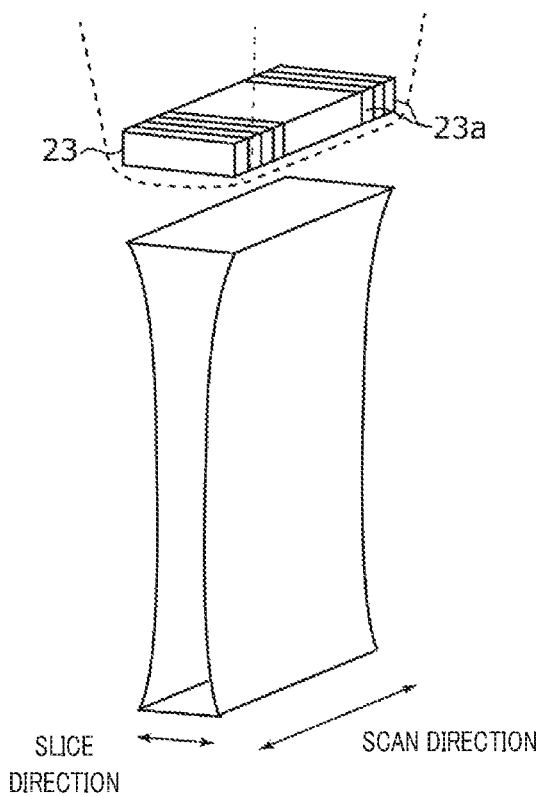
Figure 3:
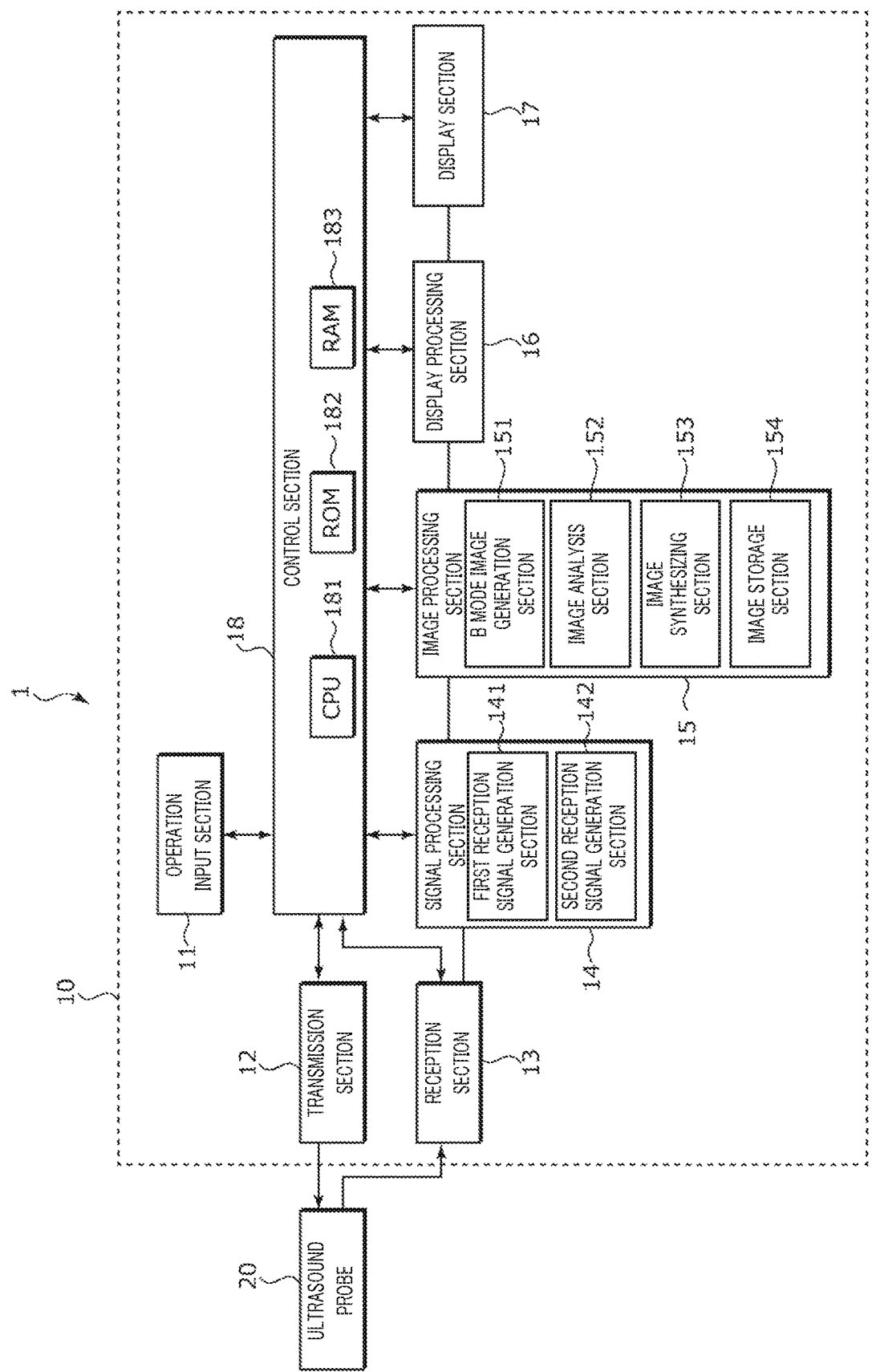
FIG. 3 is a block diagram illustrating a principal part of a control system of the ultrasound diagnostic apparatus.

FIG. 1 illustrates an external appearance of ultrasound diagnostic apparatus 1 according to an embodiment of the present invention. FIG. 2A and FIG. 2B illustrate a configuration of ultrasound probe 20. FIG. 3 is a block diagram illustrating a principal part of a control system of ultrasound diagnostic apparatus 1.

As illustrated in FIG. 1, ultrasound diagnostic apparatus 1 includes ultrasound diagnostic apparatus body 10 and ultrasound probe 20. Ultrasound diagnostic apparatus body 10 and ultrasound probe 20 are connected with each other through cable 30. Note that ultrasound probe 20 may be connected with ultrasound diagnostic apparatus body 10 by radio communication.

Ultrasound diagnostic apparatus 1 is used for image diagnosis by visualizing the shapes, properties or dynamics in the subject in the form of an ultrasound image. In particular, as its feature, ultrasound diagnostic apparatus 1 has a function of presenting, as puncture support information, authentication of the end of the puncture needle in the display image, i.e., whether the end of the puncture needle image is the actual needle point in a paracentesis of inserting a puncture needle to a target (e.g., an extraction object of a sample such as a muscle, a tendon, a nerve fascicle, a tumor and the like of a subject).

Ultrasound probe 20 transmits ultrasound to a subject and receives an ultrasound echo reflected by the subject. Ultrasound probe 20 converts the ultrasound echo into a reception signal and transmits it to ultrasound diagnostic apparatus body 10. Ultrasound probe 20 may be any electronic scanning probe such as a convex probe, a linear probe, and a sector probe, or a mechanical scanning probe such as a mechanical sector probe. Ultrasound probe 20 may include a puncture needle guide part to which a puncture needle is attached for guiding the puncturing direction.

As illustrated in FIG. 2A, ultrasound probe 20 includes acoustic lens 21, acoustic matching layer 22, transducer array 23, and bucking material 24 in this order from the ultrasound radiation side. Note that a protective layer may be disposed on a surface (ultrasound wave radiation surface) of acoustic lens 21.

Acoustic lens 21 is a lens that causes a convergence of ultrasound in a slice direction (the direction orthogonal to the scanning direction in which a plurality of transducers are arranged), and for example, in the case where a material whose sonic velocity is slower than that of the living body is used as the acoustic lens, acoustic lens 21 typically has a half cylindrical shape protruding at its center portion in the slice direction.

Acoustic matching layer 22 is an intermediate material intended for efficiently transmitting ultrasound into the subject, and performs matching between acoustic impedances of transducer 23a and the subject.

Transducer array 23 is composed of a plurality of belt-shaped transducers 23a disposed in a single line in the scanning direction. That is, ultrasound probe 20 is a so-called single-line probe.

Bucking material 24 attenuates unnecessary vibrations generated at transducer array 23.

Ultrasound probe 20 provides a beam profile of ultrasound that converges in the slice direction (see FIG. 2B). Note that convergence of ultrasound in the scanning direction may be achieved by driving transducers 23a in a switching manner (a so-called electron scanning system).

Ultrasound diagnostic apparatus body 10 visualizes the internal state of the subject in the form of an ultrasound image (B mode image) by using a reception signal from ultrasound probe 20. In the present embodiment, ultrasound diagnostic apparatus body 10 generates and displays a B mode image by utilizing a THI method.

As illustrated in FIG. 3, ultrasound diagnostic apparatus body 10 includes operation input section 11, transmission section 12, reception section 13, signal processing section 14, image processing section 15, display processing section 16, display section 17, control section 18 and the like.

Transmission section 12, reception section 13, signal processing section 14, image processing section 15 and display processing section 16, which achieve respective functions in conjunction with control section 18, are composed of dedicated or general-purpose hardware (electronic circuit), such as a digital signal processor (DSP), an application specific integrated circuit (ASIC), and a programmable logic device (PLD), in accordance with respective processes.

Operation input section 11 receives an instruction command to start a diagnosis and the like, or an input of information relating to a subject, for example. Operation input section 11 includes an operation panel having a plurality of input switches, a keyboard, a mouse and the like, for example. Note that operation input section 11 may be composed of a touch panel integrated with display section 17.

Under an instruction of control section 18, transmission section 12 generates a transmission signal (drive signal) and outputs it to ultrasound probe 20. Although not illustrated in the drawing, transmission section 12 includes a clock generation circuit, a pulse generation circuit, a pulse width setting section and a delay circuit, for example.

The clock generation circuit generates a clock signal that sets the transmission timing and/or the transmission frequency of a pulse signal. The pulse generation circuit generates a bipolar rectangular wave pulse of a preliminarily set voltage amplitude at a predetermined cycle. The pulse width setting section sets the pulse width of the rectangular wave pulse output from the pulse generation circuit. A rectangular wave pulse generated by the pulse generation circuit are separated into different wiring paths for respective transducers 23a of ultrasound probe 20 before or after the input to the pulse width setting section. The delay circuit delays the generated rectangular wave pulses in accordance with the transmission timings of respective transducers 23a, and outputs the resulting rectangular wave pulses to transducers 23a.

Under an instruction of control section 18, reception section 13 receives the reception signal from ultrasound probe 20 and outputs it to signal processing section 14. Although not illustrated in the drawing, reception section 13 includes an amplifier, an A/D conversion circuit, and a phasing addition circuit, for example.

The amplifier amplifies, by a preliminarily set amplification factor, the reception signal according to the ultrasound received by each of transducers 23a of ultrasound probe 20. The A/D conversion circuit converts the amplified reception signal into digital data at a predetermined sampling frequency. The phasing addition circuit gives, to the A/D converted reception signal, a delay time for each wiring path corresponding to each transducer 23a to rectify the time phase, and performs addition (phasing addition) of them.

Signal processing section 14 includes first reception signal generation section 141 and second reception signal generation section 142. First reception signal generation section 141 and second reception signal generation section 142 generate a first reception signal and a second reception signal from the reception signal under an instruction of control section 18. That is, signal processing section 14 functions as "reception signal acquiring section" of the embodiment of the present invention.

Figure 4:
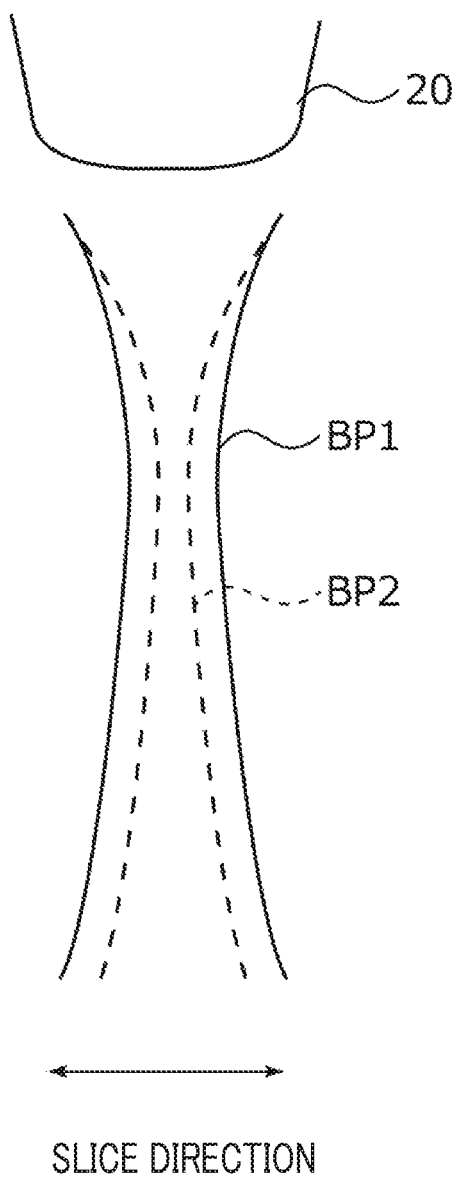
FIG. 4 illustrates a beam profile of a reception signal.

In the present embodiment, the first reception signal is a fundamental signal composed of a fundamental component of an ultrasound echo, and the second reception signal is a harmonic signal composed of a harmonic component of an ultrasound echo. As illustrated in FIG. 4, a second beam profile BP2 provided by the second reception signal (harmonic signal) has a beam width, in the slice direction, narrower than that of a first beam profile BP1 provided by the first reception signal (fundamental signal), and thus has a high resolution.

Image processing section 15 includes B mode image generation section 151, image analysis section 152, image synthesizing section 153 and image storage section 154. In addition, although not illustrated in the drawing, image processing section 15 includes a digital scan converter (DSC) that performs coordinate conversion and pixel interpolation in accordance with the type of ultrasound probe 20.

Under an instruction of control section 18, B mode image generation section 151 generates a first B mode image and a second B mode image representing the internal state of the subject on the basis of the first reception signal and the second reception signal. In the case where a puncture needle is inserted in the subject, the image of the puncture needle (a first puncture needle image and a second puncture needle image) is depicted in the first B mode image and the second B mode image.

Image analysis section 152 compares the first puncture needle image included in the first B mode image and the second puncture needle image included in the second B mode image to specify the end position of the puncture needle. Image analysis section 152 functions as "determination section" of the embodiment of the present invention.

When a puncture needle is inserted into the subject, image synthesizing section 153 generates a display image including the puncture needle, and indicates, on the display image, whether the end of the puncture needle in the display image is an actual needle point. That is, image synthesizing section 153 functions as "presenting section" of the embodiment of the present invention.

Image storage section 154 is composed of a volatile memory such as a dynamic random access memory (DRAM) or a rewritable high-speed nonvolatile memory Image storage section 154 stores image data generated by B mode image generation section 151 or image synthesizing section 153 in a frame unit. The image data stored in image storage section 154 is read under the control of control section 18, and is used for the analysis by image analysis section 152 and/or for the indication on display section 17.

Under an instruction of control section 18, display processing section 16 converts the display image data generated by image processing section 15 into a display signal corresponding to display section 17, and outputs the converted signal.

For example, display section 17 is composed of a liquid crystal display, an organic EL display, a CRT display or the like. Under an instruction of control section 18, display section 17 displays an image on the basis of the display signal of display processing section 16.

Control section 18 controls the entirety of ultrasound diagnostic apparatus 1 by controlling operation input section 11, transmission section 12, reception section 13, signal processing section 14, image processing section 15, display processing section 16 and display section 17 in accordance with their functions.

Control section 18 includes a central processing unit (CPU) 181 as a computation/control device, a read only memory (ROM) 182 and random access memory (RAM) 183 as a main storage device and the like. ROM 182 stores a basic program and/or a basic setting data. CPU 181 reads a program corresponding to processing content from ROM 182 and loads it in RAM 183, and, executes the loaded program so as to perform central control of the operations of functional blocks (transmission section 12, reception section 13, signal processing section 14, image processing section 15 and display processing section 16) of ultrasound diagnostic apparatus body 10.

In the present embodiment, functions of the functional blocks are achieved by a cooperation of each hardware of the functional blocks and control section 18. Note that part or all of the functions of the functional blocks may be achieved by execution of a program by control section 18.

Figure 5:
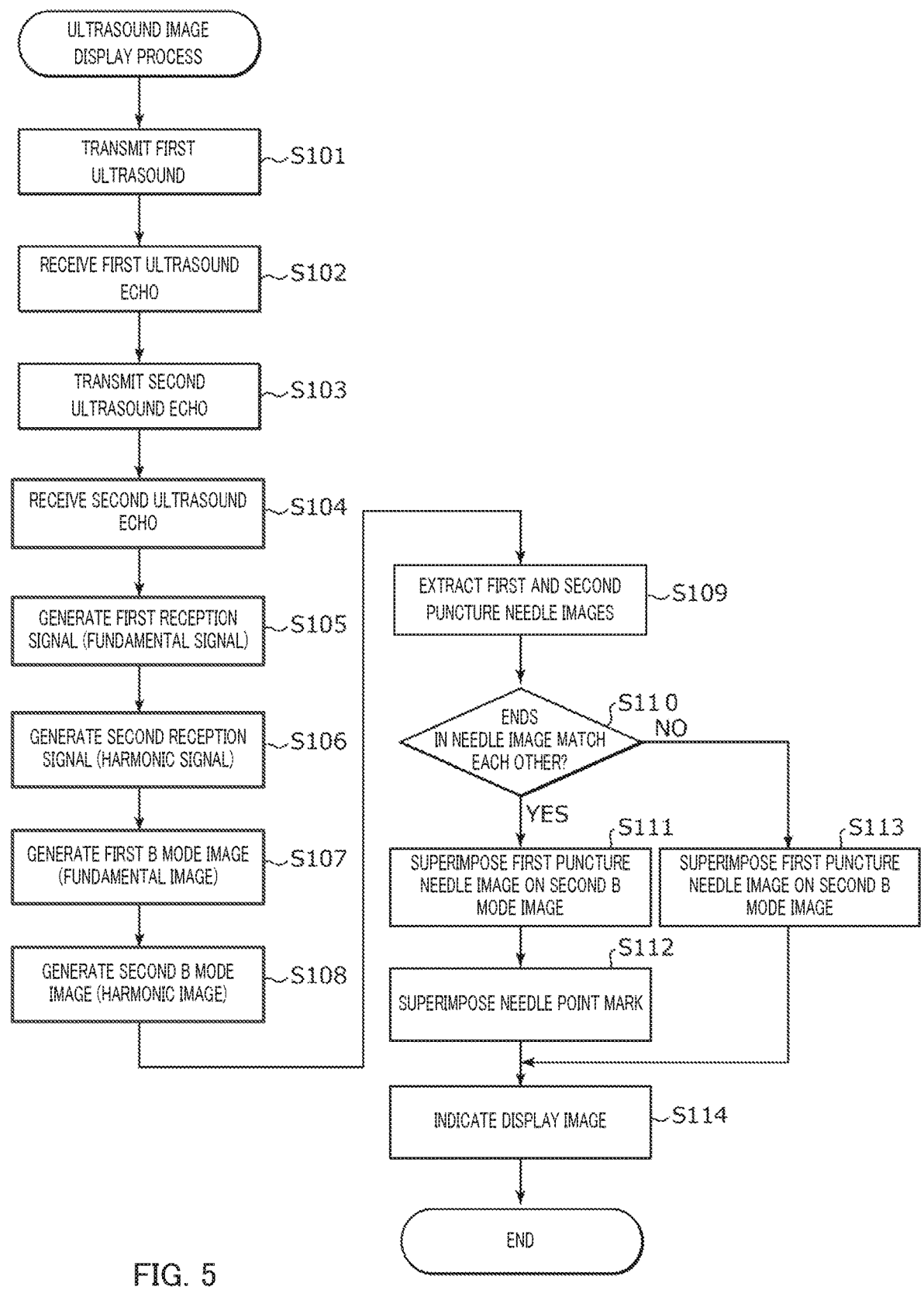
FIG. 5 illustrates an example of an ultrasound image display process.

FIG. 5 is a flowchart of an example of an ultrasound image display process of a case where ultrasound diagnostic apparatus 1 is utilized for paracentesis. For example, this process is achieved when CPU 181 executes a predetermined program (puncture support program) stored in ROM 182 in response to activation of a puncture support function in ultrasound diagnostic apparatus 1. The puncture support function is activated by selecting the diagnosis mode in operation input section 11, for example.

In the present embodiment, the following describes a case where a method typified by the pulse inversion method in which a fundamental component is diminished by a synthesis of a plurality of reception signals obtained through multiple transmissions to generate a second reception signal (harmonic signal). In the pulse inversion method, also called phase inversion method, a second transmission is performed with second ultrasound obtained by polarity inversion (phase inversion) of transmission waveform with respect to first ultrasound of a first transmission, and the fundamental component is effectively reduced by performing addition of the reception signals based on the corresponding two ultrasound echoes, thereby extracting a harmonic component having a double signal intensity.

The method of diminishing the fundamental component by using reception signals of multiple transmissions is not limited to the two-time transmission with polarity inversion, a method of synthesizing reception signals by n-time transmission with a phase shift of $\lambda/n$ (e.g., a method of synthesizing reception signals by three-time transmission with phase shifts each of which corresponds to $\lambda/3$ of the fundamental).

Further, the method of diminishing the fundamental and extracting harmonics with the multiple transmissions is not limited to the method using phase control, and it is possible to adopt an amplitude modulation method in which diminishing and extraction are performed using the dependence on the sound pressure in generation of harmonics. Specifically, it is possible to adopt a method in which a second transmission whose transmission waveform amplitude is 1/n of the transmission waveform amplitude of the first transmission is performed, and a signal obtained by multiplying the reception signal of the second transmission by n is subtracted from the reception signal of the first transmission so as to diminish the fundamental and extract harmonics.

It is assumed that ultrasound probe 20 is set such that a target is located at an approximate center in the slice direction in paracentesis. While the present invention is effective in a method in which puncturing is performed in a direction approximately parallel to the scanning direction of ultrasound probe 20 (parallel method), as well as in a method in which puncturing is performed in a direction substantially orthogonal to the scanning direction (crossing method), the present embodiment describes a case where puncturing is performed by the parallel method.

At step S101, control section 18 controls transmission section 12 to transmit first ultrasound having a center frequency of f0 from ultrasound probe 20.

At step S102, control section 18 controls reception section 13 to acquire a reception signal of a reflection wave (first ultrasound echo) corresponding to the first ultrasound received by ultrasound probe 20.

At step S103, control section 18 controls transmission section 12 to transmit, from ultrasound probe 20, second ultrasound (center frequency f0) whose polarity is inverted with respect to the first ultrasound.

At step S104, control section 18 controls reception section 13 to acquire a reception signal of a reflection wave (second ultrasound echo) corresponding to the second ultrasound received by ultrasound probe 20.

At step S105, control section 18 controls signal processing section 14 (first reception signal generation section 141) to generate a first reception signal. Specifically, a fundamental component is extracted from the reception signal of the first ultrasound echo and/or the reception signal of the second ultrasound echo to generate the first reception signal (fundamental signal). More specifically, in the case where the importance is placed on the S/N of the fundamental component, the S/N of the fundamental component may be set to the square root of 2 by subtracting the reception signal of the second ultrasound echo from the reception signal of the first ultrasound echo. The synthesizing process (subtraction process) may not be performed when the S/N of the fundamental component is sufficient, and the first reception signal may be generated by directly using the reception signal of the first or second ultrasound echo. In the case where only one of them is used, it is preferable to use the first ultrasound echo as the first reception signal, since the post processing of the first reception signal can be performed during the transmission and reception period of the second ultrasound and the signal processing load can be dispersed. Using one or both of them is not limitative, and they may be selectively switched by the user as necessary, or, may be automatically switched therebetween in accordance with the display depth and/or the gain value.

At step S106, control section 18 controls signal processing section 14 (second reception signal generation section 142) to generate the second reception signal. Specifically, the second reception signal (harmonic signal) is generated by addition and/or subtraction of the reception signal of the first ultrasound echo and the reception signal of the second ultrasound echo. In the case where odd-numbered harmonics such as third-order harmonics are extracted by subtraction, the fundamental component is also extracted, and therefore it is necessary to perform a process of removing the fundamental component with a band passage filter and the like. Further, in the case where the second reception signal is obtained through both addition and subtraction, it is preferable that a fundamental component removal process be performed on the subtraction signal, and thereafter phase adjustment be performed so as not to cause offset with the addition signal before performing the synthesizing with the addition signal.

At step S107, control section 18 controls image processing section 15 (B mode image generation section 151) to generate a first B mode image based on the first reception signal. When the puncture needle has advanced in a detection region of a first ultrasound echo, the advanced portion and the target (e.g., tendon) are depicted in the first B mode image (see FIG. 7A and FIG. 8A).

At step S108, control section 18 controls image processing section 15 (B mode image generation section 151) to generate a second B mode image based on the second reception signal. When the puncture needle has advanced in a detection region of a second ultrasound echo, the advanced portion and the target are depicted in the second B mode image (see FIG. 7B and FIG. 8B).

As illustrated in FIG. 4, the second beam profile BP2 provided by second reception signal (harmonic signal) has a beam width, in the slice direction, narrower than that of the first beam profile BP1 provided by the first reception signal (fundamental signal), and is therefore not excessively averaged in the depth direction, thus providing a high resolution. Accordingly, the second B mode image is clearer than the first B mode image. In addition, when the puncture needle is obliquely punctured, the length of the second puncture needle image to be displayed is shorter than the first puncture needle image by the reduced beam width.

At step S109, control section 18 controls image processing section 15 (image analysis section 152) to extract the first puncture needle image from the first B mode image, and the second puncture needle image from the second B mode image. The extraction of the first puncture needle image and the second puncture needle image may be performed by the method disclosed in Japanese Patent Publication No. 6044749 and the like, for example. Specifically, by subtracting, from a first smoothing image obtained by performing a smoothing process on an original image as an extraction object, a second smoothing image obtained by performing a smoothing process stronger in the horizontal direction on the original image, it is possible to extract a straight line component based on the puncture needle, i.e., the puncture needle image in which a horizontal straight line component mainly composed at the body tissue boundary is removed. In addition, a process for increasing the visibility of the puncture needle image, such as an edge detection process, a tone correction, and a binary conversion process using a threshold may be performed, and a process for increasing the detection accuracy in which the likelihood determination of the needle image is performed by a straight line extraction process such as Hough conversion may be performed.

At step S110, control section 18 controls image processing section 15 (image analysis section 152) to determine whether the end of the first puncture needle image and the end of the second puncture needle image agree with each other. For example, whether the end of the first puncture needle image and the end of the second puncture needle image agree with each other can be determined by comparison between the coordinates of the end of the first puncture needle image and the coordinates of the end of the second puncture needle image. Here, the end of first puncture needle image and the end of the second puncture needle image are ends (deeper side ends) on the side farther from the puncturing point of the puncture needle in the first B mode image and the second B mode image.

When the end of the first puncture needle image and the end of the second puncture needle image agree with each other (at step S110 "YES"), the process proceeds to step S111. When the end of the first puncture needle image and the end of the second puncture needle image do not agree with each other (at step S110 "NO"), the process proceeds to step S113. Note that when the first puncture needle image is included in the first B mode image while the second puncture needle image is not included in the second B mode image (e.g., an initial stage of puncturing in the case where the puncture needle is inserted from an end portion of the first beam profile BP1 in the slice direction), the end of the first puncture needle image may be determined as the actual needle point, and the process proceeds to step S111.

At steps S111 and S112, control section 18 controls image processing section 15 (image synthesizing section 153) to generate a display image including puncture support information. Specifically, the display image is generated by superimposing the first puncture needle image on a second B mode image clearly depicting the internal image of the subject. At this time, since the second puncture needle image is shorter than the first puncture needle image, the image is synthesized such that the second puncture needle image takes precedence over the first puncture needle image and is displayed on the front side in the puncture needle display region. In addition, as an exemplary emphatic indication, a needle point mark (in FIG. 7C "X") indicating the needle point is superimposed on the end of the puncture needle image. That is, in the present embodiment, as an exemplary determination result, an emphatic display such as a needle point mark indicates that the end of the puncture needle in the display image is the actual needle point. Note that, as another example of the emphatic display, a needle point pixel corresponding to the needle point mark or the needle point may be flashed, or the display color may be changed.

At step S113, control section 18 controls image processing section 15 (image synthesizing section 153) to generate a display image including puncture support information. The details of the process are identical to those of step S111. When the end of the first puncture needle image and the end of the second puncture needle image do not agree with each other, the emphatic display such as a needle point mark is not displayed on the display image. Specifically, in the present embodiment, as an exemplary determination result, non-display of the emphatic display such as a needle point mark indicates that whether the end of the puncture needle in the display image is the actual needle point is unclear.

While the end of the first puncture needle is the image actual needle point in the case where the end of the puncture needle is located in the detection region of the first reception signal, whether the puncture needle has passed through the detection region of the first reception signal in the slice direction cannot be determined from the first B mode image. In view of this, in the present embodiment, when the end of the first puncture needle image and the end of the second puncture needle image do not agree with each other, a warning sign indicating that whether the end of the first puncture needle is the image actual needle point is not clear is presented without presenting the emphatic display such as the needle point mark.

Here, it is preferable that color tones of the first puncture needle image and the second puncture needle image in the display image are different from each other. With such a configuration, the boundary between the first puncture needle image and the second puncture needle image is clearly indicated, and thus the operator can determine the advancing status of the puncture needle, i.e., how the puncture needle is advancing in the scanning region of the ultrasound probe 20.

At step S114, control section 18 controls display processing section 16 to display a display image on display section 17. The above-mentioned processes are repeated.

As described above, when the end of the first puncture needle image and the end of the second puncture needle image agree with each other, the emphatic display such as the needle point mark is presented in the display image. With this configuration, the operator can recognize that the position of the needle point mark is the actual needle point, and thus can efficiently perform puncturing with the display image.

On the other hand, when the end of the first puncture needle image and the end of the second puncture needle image do not agree with each other, the emphatic display such as the needle point mark is not presented in the display image. With this configuration, the operator can recognize that whether the end of the puncture needle image in the display image is the actual needle point is unclear, and accordingly the operator perform puncturing in consideration of the possibility of shifting of the end of the puncture needle with respect to the target in the slice direction, thus preventing a medical accident of wrong puncturing.

Figure 6A:
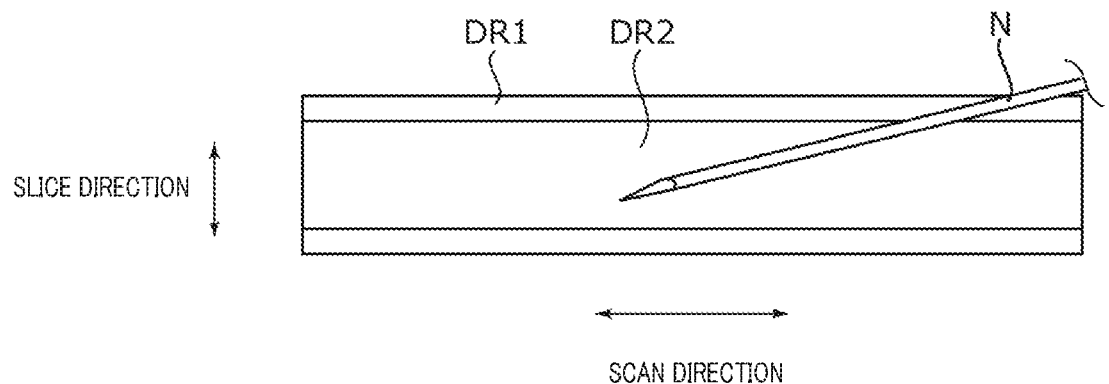
FIG. 6A and FIG. 6B illustrate an advancing status of a puncture needle with respect to a detection region.
Figure 6B:
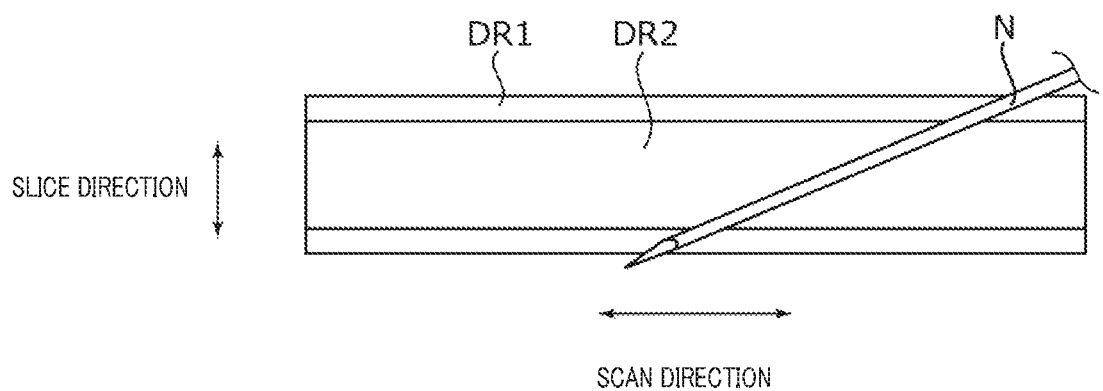

FIG. 6A and FIG. 6B are plan views illustrating a state where a puncture needle N advances in a first detection region DR1 of a first reception signal (fundamental signal) and a second detection region DR2 of a second reception signal (harmonic signal). The first detection region DR1 has a width in the slice direction wider than that of the second detection region DR2, and includes the entirety of the second detection region DR2. FIG. 6A illustrates a state where the end of puncture needle N having advanced from the first detection region DR1 is located in the second detection region DR2. FIG. 6B illustrates a state where the end of puncture needle N having advanced from the first detection region DR1 passes over the second detection region DR2, and again reaches first detection region DR1 such that the needle point does not present in second detection region DR2.

Figure 7A:
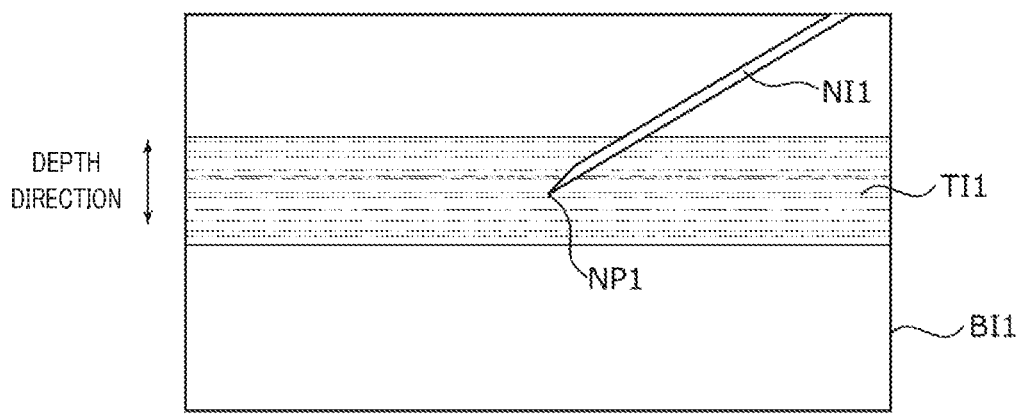
FIG. 7A to FIG. 7C illustrate examples of a first B mode image, a second B mode image and a display image.
Figure 7B:
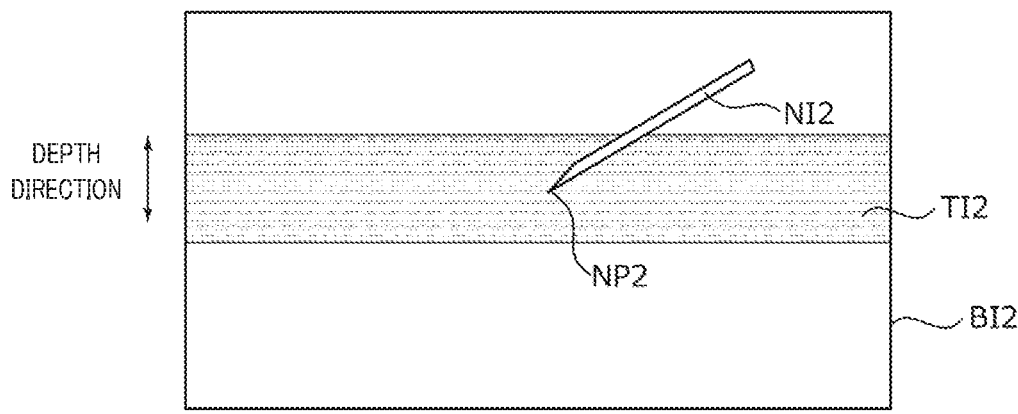
Figure 7C:
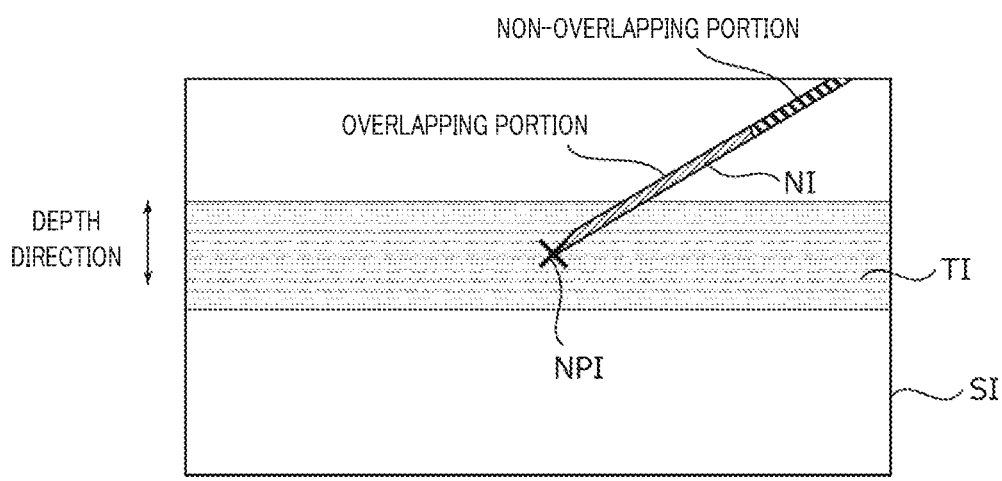

FIG. 7A to FIG. 7C illustrate a first B mode image BI1, a second mode image BI2 and a display image SI in the case where a puncture needle is inserted as illustrated in FIG. 6A.

As illustrated in FIG. 7A, the first B mode image BI1 depicts a first puncture needle image NI' and a target image TI1. In addition, as illustrated in FIG. 7B, the second B mode image BI2 depicts a second puncture needle image NI2 and a target image TI2. The second B mode image BI2 is clearer than the first B mode image BI1.

As illustrated in FIG. 6A, when the end of the puncture needle is in the second detection region DR2, the end NP1 of first puncture needle image NH and the end NP2 of the second puncture needle image NI2 agree with each other as illustrated in FIG. 7A and FIG. 7B. Accordingly, as illustrated in FIG. 7C, the display image SI, in which the first puncture needle image NH and the needle point mark NPI are superimposed on second B mode image BI2, is generated. In this case, the positions of the target and the end of the puncture needle are not shifted in the slice direction, and accordingly the operator can determine that the end of the puncture needle has reached the target when the needle point mark NPI reaches the target image TI.

Figure 8A:
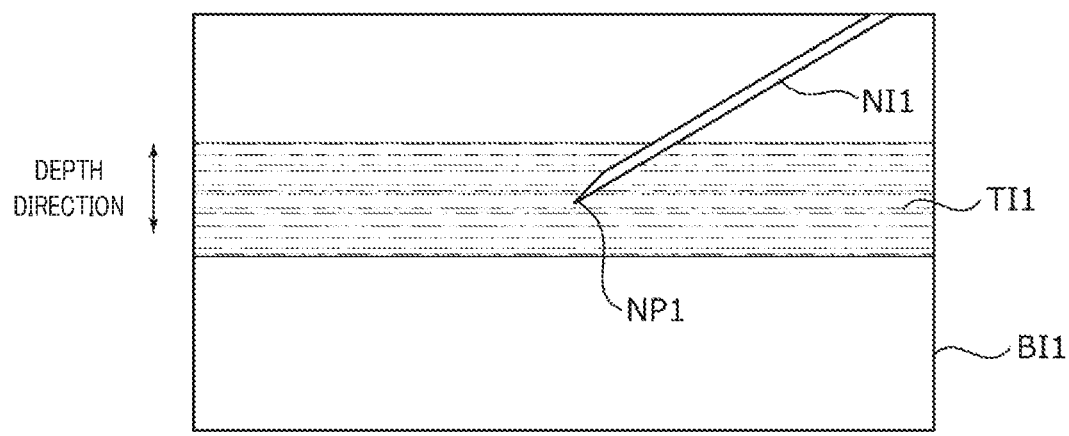
FIG. 8A to FIG. 8C illustrate other examples of the first B mode image, the second B mode image and the display image.
Figure 8B:
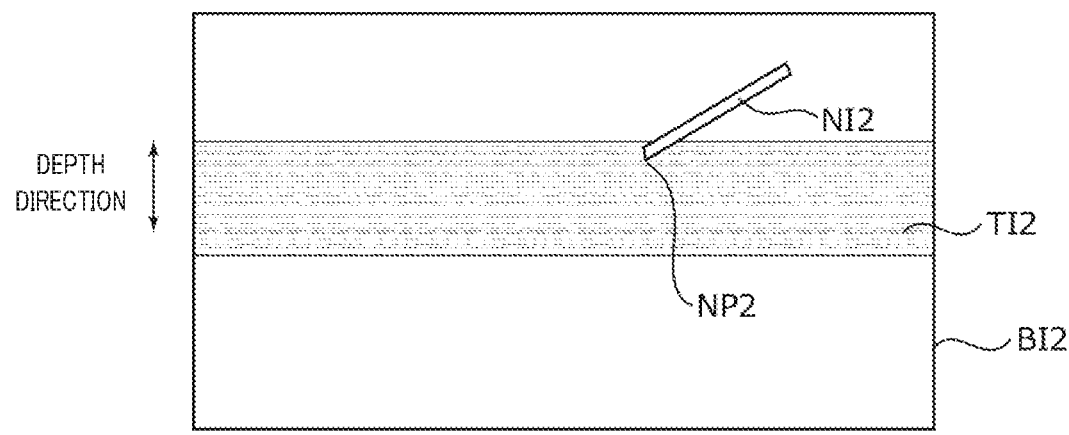
Figure 8C:
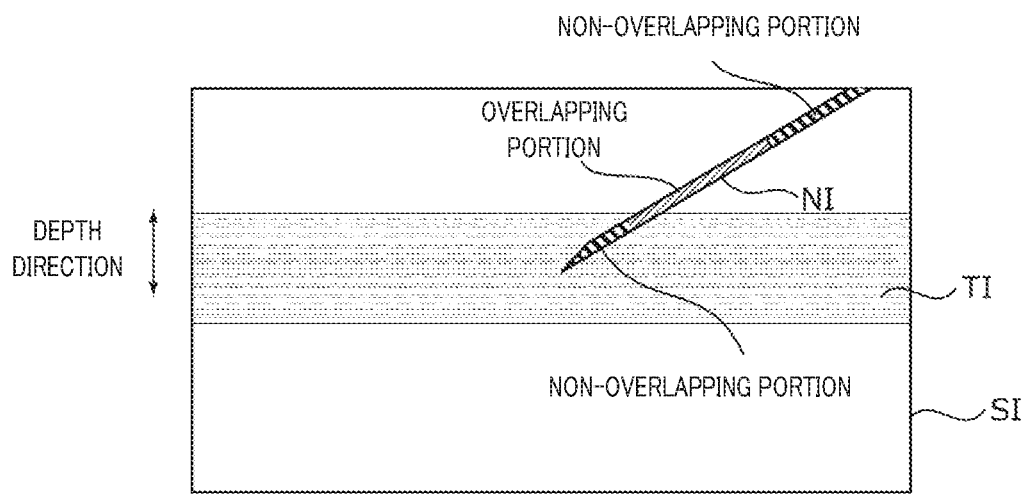

FIG. 8A to FIG. 8C illustrate a first B mode image BI1, a second mode image BI2 and a display image SI in the case where the puncture needle is inserted as illustrated in FIG. 6B.

As illustrated in FIG. 8A, the first B mode image BI1 depicts a first puncture needle image NI1 and a target image TI1. In addition, as illustrated in FIG. 8B, the second B mode image BI2 depicts a second puncture needle image NI2 and a target image TI2. The second B mode image BI2 is clearer than the first B mode image BI1. In addition, the second puncture needle image NI2 is depicted only in a portion passing over the second detection region DR2.

When the end of the puncture needle passes over the second detection region DR2 and reaches the first detection region DR1 as illustrated in FIG. 6B, the end NP1 of the first puncture needle image NI1 and the end NP2 of the second puncture needle image NI2 do not agree with each other as illustrated in FIG. 8A and FIG. 8B. Accordingly, as illustrated in FIG. 8C, the display image SI in which only the first puncture needle image ND is superimposed on the second B mode image BI2 is generated. In this case, in consideration of the possibility of shifting of the end of the puncture needle in the slice direction with respect to the target, the operator carefully performs the puncturing, or again performs puncturing from the start.

In the display images SI illustrated in FIG. 7C and FIG. 8C, the overlapping portion and the non-overlapping portion between the first puncture needle image NI1 and the second puncture needle image NI2 are indicated with different color tones, and the boundary between the first detection region DR1 and the second detection region DR2 is clearly indicated. With this configuration, the operator can determine the advancing status of the puncture needle in the slice direction.

Modification of Ultrasound Probe 20

While an ultrasound probe with an acoustic lens whose beam convergence in the slice direction is uniform is used in the above description, the configuration of the acoustic lens of the ultrasound probe may be changed such that more preferable first beam profile BP1 and second beam profile BP2 can be achieved.

Figure 9A:
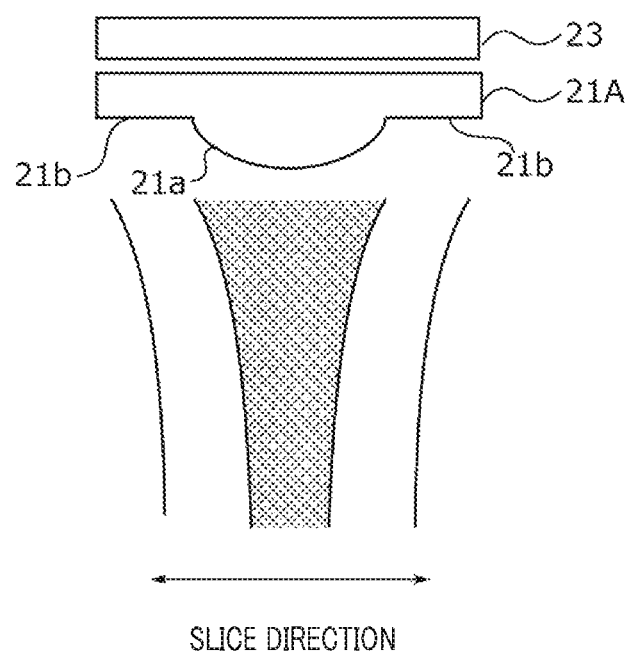
FIG. 9A and FIG. 9B illustrate an example of an acoustic lens suitable for a THI method.
Figure 9B:
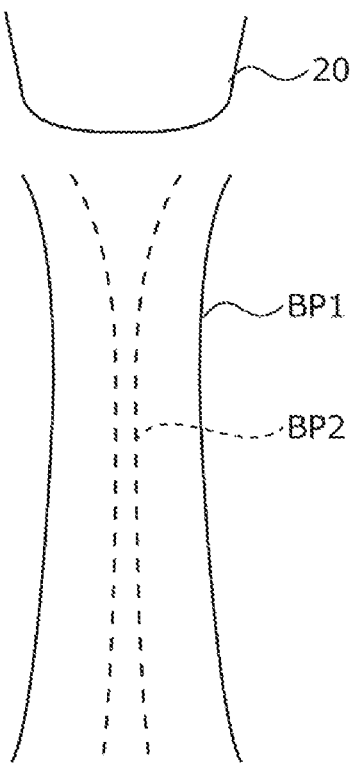

FIG. 9A and FIG. 9B illustrate an example of an acoustic lens suitable for the THI method.

Acoustic lens 21A illustrated in FIG. 9A extends across a width of each transducer 23a of the transducer array 23 and includes center portion 21a facing a center portion of each transducer 23a in the slice direction and end portion 21b facing an end portion of each transducer 23a in the slice direction, center portion 21a having a spherical shape and end portion 21b having a flat shape. Specifically, in the ultrasound wave radiation surface of acoustic lens 21A, curvatures of center portion 21a and end portion 21b in the slice direction are different from each other, and the curvature of center portion 21a is greater than that of end portion 21b. In addition, at the boundary between center portion 21a and end portion 21b, the curvature is not continuous.

In acoustic lens 21A, the convergence of end portion 21b is smaller than that of center portion 21a. That is, the ultrasound transmitted from center portion 21a of acoustic lens 21A converges in the slice direction, and accordingly the sound pressure increases, and the ultrasound echo contains a harmonic component. On the other hand, the ultrasound transmitted from end portion 21b of acoustic lens 21A do not converge in the slice direction, and the sound pressure is not increased, and accordingly, the ultrasound echo contains almost no harmonic component having sound-pressure dependence.

Accordingly, as illustrated in FIG. 9B, the difference in beam width in the slice direction in the first beam profile BP1 presented by the first reception signal composed of a fundamental component of an ultrasound echo and the second beam profile BP2 presented by the second reception signal composed of a harmonic component is greater than that of the case where the entire surface of the acoustic lens has a spherical shape (see FIG. 4) in particular in a region near the ultrasound probe. With this configuration, whether the ends of the first puncture needle image and the second puncture needle image agree with each other can be accurately determined in the entire depth region including the depth region near the ultrasound probe.

In addition, preferably, the focal length of the ultrasound transmitted from end portion 21b is non-focus (plane) or longer than the focal length of the ultrasound transmitted from center portion 21a of acoustic lens 21A.

With this configuration, the difference in beam width in the slice direction between the first beam profile BP1 and the second beam profile BP2 can be ensured while maintaining a narrow width of the second beam profile BP2 that is associated with the image quality for observation of the object, and thus the risk of losing the puncture needle can be reduced with increased minimum width and increased average width of the first beam profile BP1 while achieving increase in needle point determination accuracy.

Note that the above-described characteristics suitable for the THI method can be obtained with any acoustic lens in which the curvature change of the radiation surface in the slice direction is discontinuous between the center portion and the end portions.

Figure 10A:
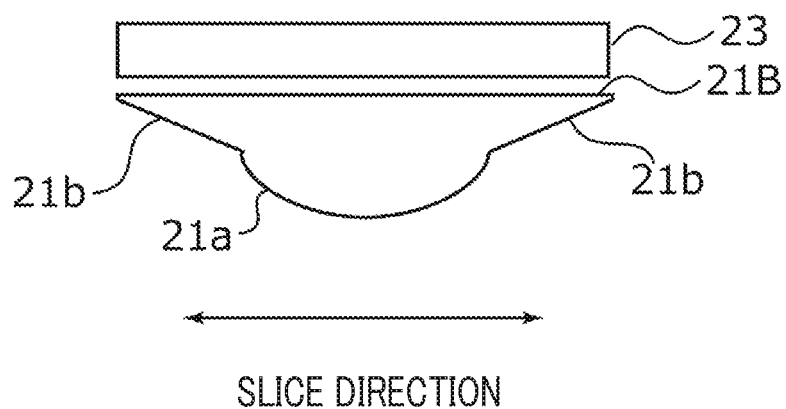
FIG. 10A and FIG. 10B illustrate an example of an acoustic lens suitable for a THI method.
Figure 10B:
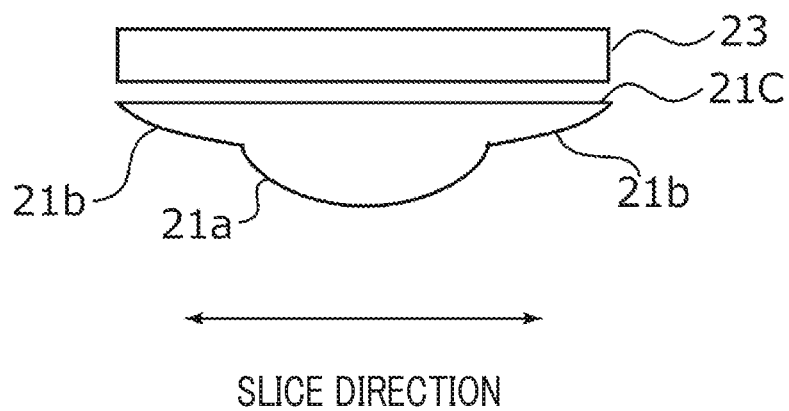

FIG. 10A and FIG. 10B illustrate another example of the acoustic lens suitable for the THI method.

End portion 21b has a flat shape in a cross-sectional view in acoustic lens 21A illustrated in FIG. 9A, whereas end portion 21b is linearly tilted in a cross-sectional view in acoustic lens 21B illustrated in FIG. 10A. In addition, in acoustic lens 21C illustrated in FIG. 10B, end portion 21b is curved in an arc-like shape in a cross-sectional view. In acoustic lens 21C, the curvature of end portion 21b is smaller than that of center portion 21a. In each of acoustic lenses 21B and 21C, the curvature of the radiation surface in the slice direction is discontinuously changed between center portion 21a and end portion 21b.

In addition, the center portion and the end portions of the transducer may have different acoustic characteristics as long as device division is not performed. For example, frequency characteristics may be substantially varied by changing the material of the backing layer disposed on the rear surface of the transducer between the center portion and the end portions, or by using materials different in decay characteristics for the center portion and the end portions of the acoustic lens, for example. In the case where the frequency characteristics are varied, it is preferable that the center frequency of the end portions is lower than that of the center portion in view of increasing the difference between the first beam profile and the second beam profile.

As described above, ultrasound diagnostic apparatus 1 according to the embodiment transmits ultrasound to a subject through ultrasound probe 20 in which a plurality of transducers 23a are disposed in a single line in the scanning direction and receives a reflection wave reflected in the subject to generate and display an ultrasound image. Ultrasound diagnostic apparatus 1 according to the embodiment includes signal processing section 14 (reception signal acquiring section) that acquires a first reception signal and a second reception signal from a reception signal obtained by ultrasound probe 20, B mode image generation section 151 that generates a first B mode image and a second B mode image on the basis of the first reception signal and the second reception signal, display processing section 16 that displays a display image on the display section on the basis of the first B mode image and the second B mode image, image analysis section 152 (determination section) that determines whether the end of the puncture needle in the display image is the actual needle point when a puncture needle is inserted into the subject, and image synthesizing section 153 (presenting section) that presents the determination result of image analysis section 152. The beam width in the slice direction of second beam profile BP2 indicated by the second reception signal is narrower than first beam profile BP1 indicted by first reception signal. Image processing section 15 presents the determination result on the basis of the first puncture needle image included in the first B mode image and the second puncture needle image included in the second B mode image.

The ultrasound image display method according to the present embodiment is a method of transmitting ultrasound to a subject through ultrasound probe 20 in which a plurality of transducers 23a are disposed in a single line in the scanning direction and receiving a reflection wave reflected in the subject to generate and display an ultrasound image. The method includes a first step of acquiring a first reception signal and a second reception signal from a reception signal obtained by ultrasound probe 20 (steps S105 and S106 in FIG. 5), a second step of generating a first B mode image and a second B mode image on the basis of the first reception signal and the second reception signal (steps S107 and S108 in FIG. 5), a third step of displaying on the image display section an image on the basis of the first B mode image and the second B mode image (step S114 in FIG. 5), a fourth step of determining whether the end of the puncture needle in the display image is the actual needle point when a puncture needle is inserted into the subject (steps S109 and S110 in FIG. 5), and a fifth step of presenting the determination result of the fourth step (at step S111 in FIG. 5 to S113). The beam width in the slice direction of second beam profile BP2 indicated by the second reception signal is narrower than first beam profile BP1 indicted by first reception signal. The fourth step presents the determination result on the basis of the first puncture needle image included in the first B mode image and the second puncture needle image included in the second B mode image.

The program according to the present embodiment is a program configured to control control section 18 (computer) of ultrasound diagnostic apparatus 1 for transmitting ultrasound to a subject through ultrasound probe 20 in which a plurality of transducers 23a are disposed in a single line in the scanning direction and receiving a reflection wave reflected in the subject to generate and display an ultrasound image to execute a first process of acquiring a first reception signal and a second reception signal from a reception signal obtained by ultrasound probe 20 (steps S105 and S106 in FIG. 5), a second process of generating a first B mode image and a second B mode image on the basis of the first reception signal and the second reception signal (steps S107 and S108 in FIG. 5), a third process of displaying on the image display section an image on the basis of the first B mode image and the second B mode image (step S114 in FIG. 5), a fourth process of determining whether the end of the puncture needle in the display image is the actual needle point when a puncture needle is inserted into the subject (steps S109 and S110 in FIG. 5), and a fifth process of presenting the determination result of the fourth step (at step S111 in FIG. 5 to S113). The beam width in the slice direction of second beam profile BP2 indicated by the second reception signal is narrower than first beam profile BP1 indicted by first reception signal. The fourth process presents the determination result on the basis of the first puncture needle image included in the first B mode image and the second puncture needle image included in the second B mode image.

This program is provided in the form of a computer-readable and transportable storage medium (such as an optical disk, an optical magnetic disc, and a memory card) in which the program is stored, for example. In addition, for example, this program may be provided by means of download from a server retaining the program through a network.

According to ultrasound diagnostic apparatus 1, the ultrasound image display method and the program according to the embodiment, an inexpensive and highly versatile single-line probe can be used, and whether the end of the puncture needle image included in the display image is the actual needle point of the puncture needle, that is, the authentication of the needle point in the display image, can be readily determined. Accordingly, ultrasound diagnostic apparatus 1 is very useful for preventing medical accidents of wrong puncturing and/or biopsy errors.

In addition, in ultrasound diagnostic apparatus 1, image synthesizing section 153 (presenting section) displays the determination result on the display image.

With this configuration, the operator can visually recognize whether the end of the puncture needle image included in the display image is the actual needle point of the puncture needle.

In addition, in ultrasound diagnostic apparatus 1, image synthesizing section 153 (presenting section) compares the first puncture needle image and the second puncture needle image to determine the end position of the puncture needle, and displays the determined end of the puncture needle image in an emphasis manner.

With this configuration, by means of emphatic display, the operator can readily recognize whether the end of the puncture needle image included in the display image is the actual needle point of the puncture needle.

In addition, in ultrasound diagnostic apparatus 1, image synthesizing section 153 (presenting section) displays the second B mode image and the first puncture needle image in a synthesized manner.

With this configuration, a long puncture needle image is depicted on a clear second B mode image, and thus the operator can easily determine the advancing status of the puncture needle.

In addition, in ultrasound diagnostic apparatus 1, image synthesizing section 153 (presenting section) displays the first puncture needle image and the second puncture needle image such that an overlapping portion and a non-overlapping portion of the first puncture needle image and the second puncture needle image are displayed in different color tones.

With this configuration, the boundary between the first detection region DR1 and the second detection region DR2 is clearly depicted, and the operator can more specifically determine the advancing status of the puncture needle in the slice direction.

In addition, in ultrasound diagnostic apparatus 1, the beam centers of the first beam profile BP1 and the second beam profile BP2 in the slice direction are identical.

With this configuration, in the slice direction, first detection region DR1 is uniformly formed on both sides of second detection region DR2, and thus the advancing status of the puncture needle suitable can be determined regardless of the puncturing point.

In addition, in ultrasound diagnostic apparatus 1, signal processing section 14 (reception signal acquiring section) generates the first reception signal on a basis of a fundamental component included in the reception signal, and generates the second reception signal on a basis of a harmonic component included in the reception signal. Specifically, in ultrasound diagnostic apparatus 1, signal processing section 14 generates the first reception signal and the second reception signal by a THI method.

With this configuration, the first reception signal and the second reception signal can be readily acquired such that the beam width in the slice direction differs in the beam profile.

In addition, in ultrasound diagnostic apparatus 1, signal processing section 14 (reception signal acquiring section) generates the second reception signal by a pulse inversion method.

With this configuration, the fundamental component is offset and the harmonic component is emphasized, and thus, the second reception signal can be acquired without degrading the distance resolution.

Also, the following invention is disclosed in the present embodiment.

Specifically, ultrasound probe 20 according to the embodiment transmits and receives ultrasound, and includes transducer array 23 in which a plurality of transducers 23*a* are disposed in a single line in the scanning direction, and acoustic lenses 21A, 21B and 21C disposed on the ultrasound radiation side of transducer array 23. In acoustic lenses 21A, 21B and 21C, the curvature of center portion 21*a* of a radiation surface and a curvature of end portion 21*b* of the radiation surface differ in the slice direction in a discontinuous manner, and the curvature of center portion 21*a* is greater than the curvature of end portion 21*b*. In addition, the curvature is discontinuous at the boundary between center portion 21*a* and end portion 21*b*.

Specifically, the convergence of the ultrasound radiated from end portion 21*b* is smaller than the convergence of the ultrasound radiated from center portion 21*a* of acoustic lenses 21A, 21B and 21C.

With this configuration, in the case where the first reception signal and the second reception signal are acquired by the THI method, the difference in beam width in the slice direction between first beam profile BP1 indicted by first reception signal and second beam profile BP2 indicated by the second reception signal is greater than the case where the entire surface of acoustic lens 21 has a spherical shape (see FIG. 4), in particular in a region near the ultrasound probe. Accordingly, it is possible to accurately determine whether the ends of the first puncture needle image and the second puncture needle image agree with each other in the entire depth region including the depth region near the ultrasound probe.

In addition, in ultrasound probe 20, the focal length the ultrasound transmitted from center portion 21a of acoustic lenses 21A, 21B and 21C is a non-focus (plane) or longer than the focal length of ultrasound transmitted from end portion 21b.

With this configuration, the difference in beam width in the slice direction between the first beam profile BP1 and the second beam profile BP2 can be ensured while maintaining a narrow width of the second beam profile BP2 that is associated with the image quality for observation of the object, and thus the risk of losing the puncture needle can be reduced with increased minimum width and increased average width of the first beam profile BP1 while achieving increase in needle point determination accuracy.

Further, in acoustic lenses 21A, 21B and 21C, center portion 21a and end portion 21b may have different acoustic characteristics. For example, by using a lens material whose decay characteristics is high for end portion 21b with respect to center portion 21a, transmission of the high-frequency component that tends to generate harmonic generate can be suppressed, and harmonics can be more selectively generated in the second beam profile BP2.

While the invention made by the present inventor has been specifically described based on the preferred embodiments, it is not intended to limit the present invention to the above-mentioned preferred embodiments but the present invention may be further modified within the scope and spirit of the invention defined by the appended claims.

For example, while the first reception signal composed of the fundamental component and the second reception signal composed of the harmonic component are generated by the pulse inversion method in the embodiment, the second reception signal composed of the harmonic component may be generated by a filtering method. With the filtering method, in the case where ultrasound having center frequency f0 is transmitted, the 2f0 harmonic component is extracted from the reception signal with use of a 2f0-pass filter.

In addition, ultrasound of two types differing in beam width in the slice direction in the beam profile may be transmitted and received so as to use the reception signals as the first reception signal and the second reception signal.

In addition, the second B mode image and the first puncture needle image may be displayed in a synthesized manner without presenting the emphatic display such as the needle point mark on the display image. In this case, by preliminarily understanding that the end of the puncture needle image corresponds to the actual needle point only when the end of the first puncture needle image and the end of the second puncture needle image agree with each other in the display image, the operator can recognize whether the end of the puncture needle in the display image is the actual needle point. Note that, while the determination whether the end of the puncture needle image is the actual needle point depends on the operator, the basis of the determination is presented by the display image.

While the results of the determination whether the end of the puncture needle in the display image is the actual needle point is visually presented in the form of the display image in the embodiment, the results may be presented in an auditory form.

Although embodiments of the present invention have been described and illustrated in detail, the disclosed embodiments are made for purpose of illustration and example only and not limitation. The scope of the present invention should be interpreted by terms of the appended claims.

What is claimed is:

1. An ultrasound diagnostic apparatus that transmits ultrasound to a subject through an ultrasound probe in which a plurality of transducers are disposed in a single line in a scanning direction and receives a reflection wave reflected in the subject to generate and display an ultrasound image, the ultrasound diagnostic apparatus comprising a hardware processor configured to
   acquire a first reception signal and a second reception signal from an ultrasound reception signal obtained by the ultrasound probe, wherein the first reception signal is based on a fundamental component included in the ultrasound reception signal, and the second reception signal based on a harmonic component included in the ultrasound reception signal;
   generate a first B mode image including a first puncture needle image based on the first reception signal and a second B mode image including a second puncture needle image based on the second reception signal;
   display a display image on a display section on a basis of the first B mode image and the second B mode image;
   determine whether an end of a puncture needle in the display image is an actual end of the puncture needle when the puncture needle is inserted into the subject by determining whether the end positions of the first puncture needle image and the second puncture needle image match each other; and
   present a determination result based on the first puncture needle image and the second puncture needle image, wherein
   a beam width in a slice direction of a second beam profile indicated by the second reception signal is narrower than that of a first beam profile indicated by the first reception signal.

2. The ultrasound diagnostic apparatus according to claim 1, wherein the hardware processor displays the determination result on the display image.

3. The ultrasound diagnostic apparatus according to claim 2, wherein
   when end positions of the first puncture needle image and the second puncture needle image match each other, the hardware processor determines that the end positions are the actual end of the puncture needle, and displays the end position thus determined in an emphasized manner.

4. The ultrasound diagnostic apparatus according to claim 2, wherein the hardware processor displays the second B mode image and the first puncture needle image in a synthesized manner.

5. The ultrasound diagnostic apparatus according to claim 4, wherein the hardware processor displays the first puncture needle image and the second puncture needle image such that an overlapping portion and a non-overlapping portion of the first puncture needle image and the second puncture needle image are displayed in different color tones.

6. The ultrasound diagnostic apparatus according to claim 1, wherein beam centers of the first beam profile and the second beam profile in the slice direction are identical.

7. The ultrasound diagnostic apparatus according to claim 1, wherein the hardware processor generates the second reception signal by a pulse inversion method.

8. The ultrasound diagnostic apparatus according to claim 1, further comprising the ultrasound probe, wherein the ultrasound probe includes an acoustic lens in which a curvature of a radiation surface in the slice direction discontinuously changes between a center portion and an end portion of the radiation surface.

9. An ultrasound image display method in which ultrasound is transmitted to a subject through an ultrasound probe in which a plurality of transducers are disposed in a single line in a scanning direction, and a reflection wave reflected in the subject is received to generate and display an ultrasound image, the method comprising:

acquiring a first reception signal and a second reception signal from an ultrasound reception signal obtained by the ultrasound probe, wherein the first reception signal is based on a fundamental component included in the ultrasound reception signal, and the second reception signal based on a harmonic component included in the ultrasound reception signal;

generating a first B mode image including a first puncture needle image based on the first reception signal and a second B mode image including a second puncture needle image based on the second reception signal;

displaying a display image on a display section on a basis of the first B mode image and the second B mode image;

determining whether an end of a puncture needle in the display image is an actual end of the puncture needle when the puncture needle is inserted into the subject by determining whether the end positions of the first puncture needle image and the second puncture needle image match each other; and presenting a determination result of the determining based on the first puncture needle image and the second puncture needle image, wherein a beam width in a slice direction of a second beam profile indicated by the second reception signal is narrower than a first beam profile indicated by the first reception signal.

10. An ultrasound probe configured to transmit and receive ultrasound, the ultrasound probe comprising:

a transducer array in which a plurality of transducers are disposed in a single line in a scanning direction;

an acoustic lens disposed on an ultrasound radiation side of the transducer array, the acoustic lens having a front surface facing away from the transducer;

wherein the front surface includes a center portion and end portions on opposing sides of the center portion in a slice direction, which is orthogonal to the scanning direction, the center portion having a spherical shape and each of the end portions having a flat shape; and wherein a curvature of a radiation surface of the acoustic lens is discontinuous at a boundary between the center portion and each of the end portions of the radiation surface in the slice direction, and a difference in beam width in the slice direction between a first beam profile of a first reception signal composed of a fundamental component of an ultrasound echo and a second beam profile of a second reception signal composed of a harmonic component is greater than a case where the entire surface of the acoustic lens has a spherical shape.

11. The ultrasound probe according to claim 10, wherein a convergence of ultrasound waves emitted from the end portions of the probe is less than than a convergence of ultrasound waves emitted from the center portion of the probe.

12. The ultrasound probe according to claim 10, wherein a focal length of ultrasound waves emitted from the end portions of the probe is greater than a focal length of ultrasound waves emitted from the center portion of the probe.

13. An ultrasound diagnostic apparatus comprising the ultrasound probe according to claim 10.

14. The ultrasound probe according to claim 10, wherein the acoustic lens extends across a width of each transducer of the plurality of transducers in the slice direction, the center portion of the acoustic lens faces a center portion of the each transducer in the slice direction, and the end portions of the acoustic lens faces end portions of the each transducer in the slice direction.

15. The ultrasound probe according to claim 10, wherein ultrasound waves emitted from the center portion converge in the slice direction and ultrasound waves emitted from the end portions do not converge in the slice direction.

* * * * *